United States Patent
Chuang et al.

(10) Patent No.: US 10,130,252 B2
(45) Date of Patent: Nov. 20, 2018

(54) TRIAL FRAME AND METHOD FOR MEASURING KEY PARAMETER THEREOF

(71) Applicant: NATIONAL CHIAO TUNG UNIVERSITY, Hsinchu (TW)

(72) Inventors: Jen-Hui Chuang, Hsinchu (TW); Yi-Yu Hsieh, Miaoli County (TW); Yen-Shuo Lin, Tainan (TW)

(73) Assignee: NATIONAL CHIAO TUNG UNIVERSITY, Hsinchu (TW)

( * ) Notice: Subject to any disclaimer, the term of this patent is extended or adjusted under 35 U.S.C. 154(b) by 44 days.

(21) Appl. No.: 14/481,901

(22) Filed: Sep. 9, 2014

(65) Prior Publication Data

US 2015/0359423 A1 Dec. 17, 2015

(30) Foreign Application Priority Data

Jun. 11, 2014 (TW) .............................. 103120868 A

(51) Int. Cl.
| | | |
|---|---|---|
| *A61B 3/04* | (2006.01) | |
| *G02C 5/00* | (2006.01) | |
| *A61B 3/00* | (2006.01) | |
| *A61B 3/14* | (2006.01) | |
| *A61B 3/02* | (2006.01) | |
| *G02C 13/00* | (2006.01) | |

(52) U.S. Cl.
CPC .............. *A61B 3/04* (2013.01); *G02C 13/003* (2013.01)

(58) Field of Classification Search
CPC ........... A61B 3/04; A61B 3/024; A61B 3/103; A61B 3/18; A61B 3/1015; A61B 3/14; A61B 3/152; A61B 3/113; A61B 3/1225; A61B 3/0321; G02C 5/00; G02C 13/005
USPC ........ 351/227, 222, 200, 228–231, 245–246, 351/41, 204–206, 208–210, 221, 223
See application file for complete search history.

(56) References Cited

U.S. PATENT DOCUMENTS

| | | | | |
|---|---|---|---|---|
| 2,659,266 | A | | 11/1953 | Swisher |
| 6,132,045 | A | * | 10/2000 | Gauvreau ............ G02C 13/005 351/200 |
| 7,588,335 | B2 | * | 9/2009 | Kubitza ............... G02C 13/005 351/200 |
| 8,220,923 | B2 | | 7/2012 | Saffra |
| 2002/0003603 | A1 | | 1/2002 | Bullard |
| 2009/0153792 | A1 | | 6/2009 | Lee |
| 2009/0262302 | A1 | * | 10/2009 | Chauveau ............ G02C 13/005 351/204 |

* cited by examiner

*Primary Examiner* — Dawayne A Pinkney
(74) *Attorney, Agent, or Firm* — CKC & Partners Co., Ltd.

(57) ABSTRACT

A trial frame includes a trial frame body and at least one measurement subject having a visual invariant geometric characteristic. The trial frame body has at least one key parameter. The measurement subject is disposed on the trial frame body and collaborates with a measurement method. A two-dimensional image of the measurement subject is recorded by an image capturing device when the trial frame body fits to a user, and the key parameter is deduced from the two-dimensional image of the measurement subject.

11 Claims, 13 Drawing Sheets

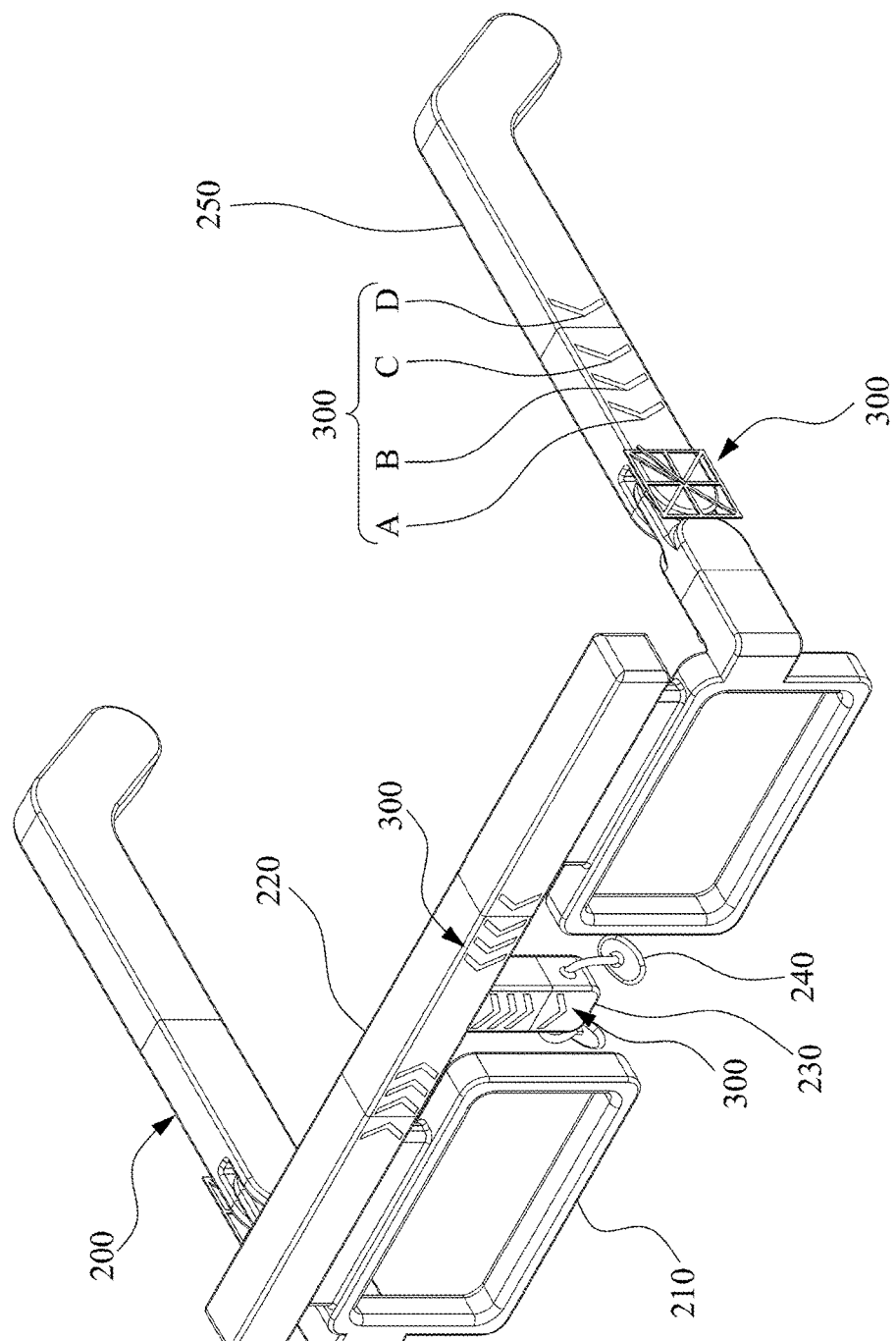

TRIAL FRAME AND METHOD FOR MEASURING KEY PARAMETER THEREOF

RELATED APPLICATIONS

This application claims priority to Taiwanese Application Serial Number 103120868, filed Jun. 17, 2014, which are herein incorporated by reference.

BACKGROUND

When a consumer is prescribed with glasses, because each person's pupil distance, head shape, and face shape are different, a trial frame is needed to measure associated information to make the glasses perfectly fit to the consumer.

A professional optometrist is required for using the trial frame, so as to correctly read data of the trial frame. Therefore, if desiring a highly customized frame, the consumer not only has to pay a higher fee, but also has to attend a specific location at which the optometrist is on duty.

SUMMARY

This disclosure provides a trial frame working with a measurement method to easily and fast measure a key parameter of the trial frame.

In one aspect of the disclosure, a trial frame is provided. The trial frame includes a trial frame body and at least one measurement subject having a visual invariant geometric characteristic. The trial frame body has at least one key parameter. The measurement subject is disposed on the trial frame body and collaborating with a measurement method. A two-dimensional image of the measurement subject is recorded by an image capturing device when the trial frame body fits to a user, and the key parameter is deduced from the two-dimensional image of the measurement subject.

In one or more embodiments, the trial frame body includes a pair of eyewires, a pair of nose rests, and a pair of temples. The nose rests are connected to the eyewires. The temples include a pair of connecting portion and a pair of ear portions. The connecting portions are connected to the eyewires. The ear portions are moveably connected to the connecting portions respectively. The measurement subject includes a fixed point A, a fixed point B, a fixed point C, and a moving point D. The fixed points A, B, and C are disposed on one of the connecting portions with equal intervals between each other, and the moving point D is disposed on one of the ear portions. The points A, B, C, and the moving point D are disposed on the same straight line.

In one or more embodiments, the trial frame body includes a pupil distance measurement ruler, a pair of eyewires, a pair of nose rests, and a pair of temples. The pupil distance measurement ruler includes a fixed portion and a pair of moving portions movably connected to the fixed portion. The eyewires are respectively connected to the moving portions. The nose rests are connected to the eyewires. The temples are connected to the eyewires. The measurement subject includes a fixed point A, a fixed point B, a fixed point C, and a moving point D. The fixed points A, B, and C are disposed on the fixed portion with equal intervals between each other, and the moving point D is disposed on one of the moving portions. The points A, B, C, and the moving point D are disposed on the same straight line.

In one or more embodiments, the trial frame body includes a support bar, a pair of eyewires, a nose bridge measurement ruler, a pair of nose rests, and a pair of temples. The eyewires are respectively connected to two ends of the support bar. The nose bridge measurement ruler is connected to a central portion of the support bar and includes a fixed portion and a moving portion connected to the fixed portion. The nose rests are connected to the moving portion. The temples are connected to the eyewires. The measurement subject includes a fixed point A, a fixed point B, a fixed point C, and a moving point D. The fixed points A, B, and C are disposed on the fixed portion with equal intervals between each other, and the moving point D is disposed on the moving portion. The points A, B, C, and the moving point D are disposed on the same straight line.

In one or more embodiments, the trial frame body includes a pair of temples, a pair of eyewires, and a pair of nose rests. The eyewires are rotatably connected to the temples. The nose rests are respectively connected to the eyewires. The measurement subject is an angle measuring module fixed to the temples. The angle measuring module includes a fixed portion and a moving portion connected to the fixed portion. The angle measuring module includes a fixed point A, a fixed point B, a fixed point C, a moving point D, and a fixed point O. The fixed points A, B, and C are disposed on the fixed portion with equal intervals between each other, and the points A, B, and C are disposed on the same straight line. The fixed point O is disposed on the fixed portion, and angles ∠AOB and ∠BOC have the same magnitudes. The moving portion has a first end and a second end. The first end of the moving portion is connected to the fixed point O. The moving point D is disposed on the second end of the moving portion. The second end is movably connected to the fixed portion. The connection portion of the second end and the fixed portion, and the fixed points A, B, and C are disposed on the same straight line. The moving portion is fixed to the eyewires, such that when the eyewires are rotated with respect to the temples, the moving point D moves with respect to the fixed portion, and an angle between the moving portion and the eyewires is fixed.

In one or more embodiments, the trial frame body includes a pair of temples, a pair of eyewires, a pair of nose rests, and an angle measuring module. The eyewires are rotatably connected to the temples. The nose rests are respectively connected to the eyewires. The angle measuring module provides an information showing an angle relationship between the temples and the eyewires.

In another aspect of the disclosure, a method for measuring a key parameter of a trial frame is provided. The method includes: putting the trial frame having at least one measurement subject on a user's head, in which the measurement subject has a visual invariant geometric characteristic which deduces a value corresponding to the key parameter of the trial frame; adjusting the key parameter of the trial frame for fitting the trial frame to the user; recording a two-dimensional image of the measurement subject by an image capturing device; and deducing the value corresponding to the key parameter of the trial frame according to the two-dimensional image of the measurement subject, thereby determining the key parameter.

In one or more embodiments, a cross ratio of the measurement subject is deduced by using the two-dimensional image of the measurement subject, such that the measurement subject has the visual invariant geometric characteristic.

In one or more embodiments, the measurement subject includes a fixed point A, a fixed point B, a fixed point C, and a moving point D. The cross ratio R is deduced from the following mathematical relationship:

$$R = \frac{\overline{ABCD}}{\overline{BCAD}}$$

In one or more embodiments, the trial frame includes a fixed portion and a moving portion. A spatial configuration of the fixed portion and the moving portion determines the key parameter of the trial frame. The fixed points A, B, and C are disposed on the fixed portion with equal intervals between each other, and the moving point D is disposed on the moving portion. The points A, B, C, and the moving point D are disposed on the same straight line.

By disposing the measurement subject having the visual invariant geometric characteristic on the trial frame body, the key parameter of the trial frame can be deduced by using the two-dimensional image of the measurement object recorded by the image capturing device when the trial frame fits to the user. Therefore, the consumer who desires to prescribe glasses does not need to attend a specific place at which an optometrist is on duty for measuring the key parameter of the trial frame. By transmitting some pictures of the trial frame to the computer, the key parameter can be obtained, and the fee for prescribing glasses can be lowered as well.

It is to be understood that both the foregoing general description and the following detailed description are by examples, and are intended to provide further explanation of the invention as claimed.

BRIEF DESCRIPTION OF THE DRAWINGS

The invention can be more fully understood by reading the following detailed description of the embodiment, with reference made to the accompanying drawings as follows:

FIG. 1 is a perspective view of a trial frame according to one embodiment of this invention;

DETAILED DESCRIPTION

Figure 2A:
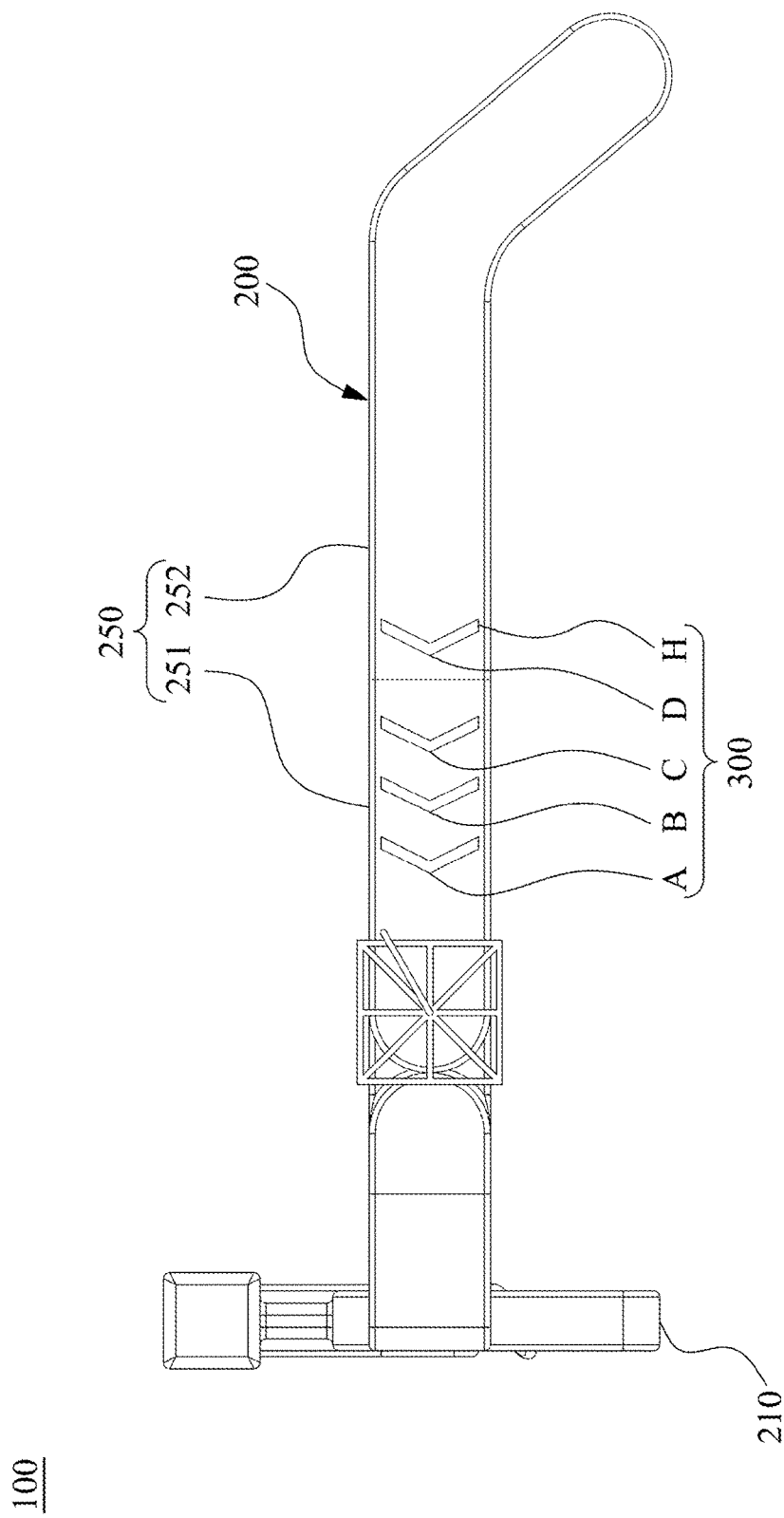
FIG. 2A is a side view of FIG. 1.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically depicted in order to simplify the drawings.

FIG. 1 is a perspective view of a trial frame 100 according to one embodiment of this invention. As shown in FIG. 1, a trial frame 100 is provided. The trial frame 100 includes a trial frame body 200 and at least one measurement subject 300 having a visual invariant geometric characteristic. The trial frame body 200 has at least one key parameter. The measurement subject 300 is disposed on the trial frame body 200 and collaborates with a measurement method. A two-dimensional image of the measurement subject 300 is recorded by an image capturing device when the trial frame body 200 fits to a user, and the key parameter of the trial frame body 200 is deduced from the two-dimensional image of the measurement subject 300.

Specifically, the trial frame body 200 may further include a pair of eyewires 210, a pupil distance measurement ruler 220, a nose bridge measurement ruler 230, a pair of nose rests 240, and a pair of temples 250. The eyewires 210 is connected to the pupil distance measurement ruler 220. The pupil distance measurement ruler 220 is connected to the nose bridge measurement ruler 230. The nose bridge measurement ruler 230 is connected to the nose rests 240. The temples 250 are connected to the eyewires 210. The pupil distance measurement ruler 220 may be used as a support bar.

FIG. 2A is a side view of FIG. 1. As shown in FIG. 2A, the temples 250 include a pair of connecting portion 251 and a pair of ear portions 252. The connecting portions 251 are connected to the eyewires 210. The ear portions 252 are moveably connected to the connecting portions 251 respectively.

The measurement subject 300 may include a fixed point A, a fixed point B, a fixed point C, and a moving point D. The fixed points A, B, and C are disposed on one of the connecting portions 251 with equal intervals between each other, and the moving point D is disposed on one of the ear portions 252. The points A, B, C, and D are disposed on the same straight line. Embodiments of this disclosure are not limited thereto. In other embodiments, the number of the measurement subjects 300 may be two, and the measurement subjects 300 may be disposed on two different temples 250 at the same time.

Arrowhead patterns H are disposed around all of the points A, B, C, and D, and the points A, B, C, and D are disposed at vertices of the respective arrowhead patterns H.

Because the points A, B, C, and D are dispose on the same straight line, a cross ratio of the measurement subject 300 may be deduced by using the spatial configuration of the measurement subject 300 in the real space or the coordinates of the configuration of the measurement subject 300 measured from the two-dimensional image of the measurement subject 300 recorded by the image capturing device. The cross ratio R is deduced from the following mathematical relationship:

$$R = \frac{\overline{ABCD}}{\overline{BCAD}}$$

The cross ratio R of the measurement subject 300 is the same whenever the cross ratio R is deduced by using the spatial configuration of the measurement subject 300 in the real space or by using the coordinates of the configuration of the measurement subject 300 measured from the two-dimensional image of the measurement subject 300 recorded by the image capturing device. The cross ratio R is the same even when the recording angle or the recording distance of the image capturing device is changed. For example, assuming that FIG. 1 and FIG. 2A both are the two-dimensional image of the measurement subject 300 on the temples 250, the cross ratio R deduced by using the coordinates of the configuration of the measurement subject 300 on FIG. 1, the cross ratio R deduced by using the coordinates of the configuration of the measurement subject 300 on FIG. 2A, and the cross ratio R deduced by using the spatial configuration of the measurement subject 300 in the real space are the same, which are referred to as the visual invariant geometric characteristic. In other words, the measurement subject 300 has the visual invariant geometric characteristic.

Figure 2B:
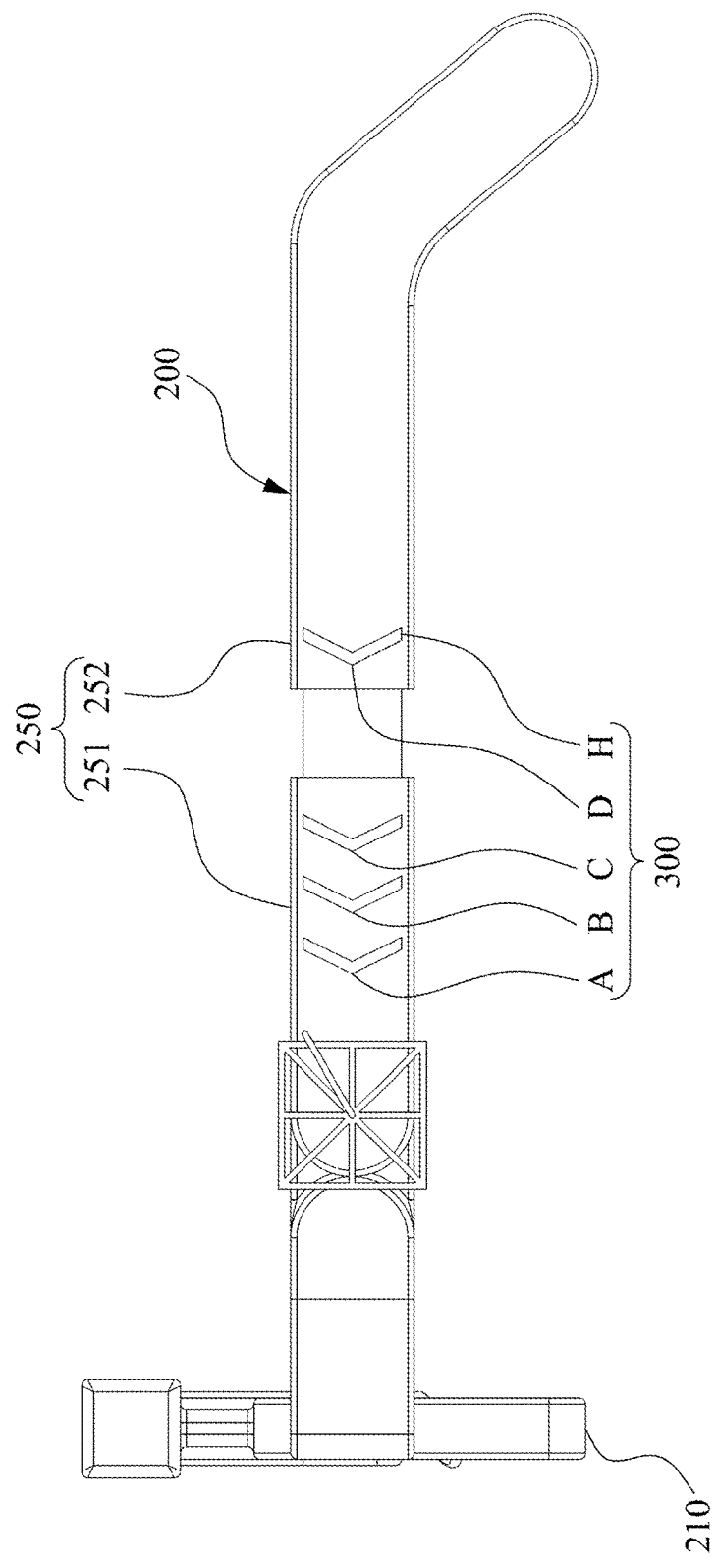
FIG. 2B is a side view of the trial frame of FIG. 1 when temples are extended.

FIG. 2B is a side view of the trial frame 100 of FIG. 1 when temples 250 are extended. As shown in FIG. 2A and FIG. 2B, when lengths of the temples 250 fitting to the user (one of the key parameters of the trial frame body 200) are measured, the user wearing the trial frame 100 may move the ear portion 252 to adjust the lengths of the temples 250, and the spatial relationship between the moving point D and the other points may be changed. Then, the cross ratio R can be deduced by using the two-dimensional image of the measurement subject 300 recorded by the image capturing device. Because the spatial relationship among the fixed point A, the fixed point B, and the fixed point C is known, the spatial relationship between the moving point D and the other points can be deduced if a value of the cross ratio R is known. Then, the lengths of the temples 250 fitting to the user are obtained.

Through the aforementioned measuring process, the consumer who desires to have a customized frame (the user) only needs to wear the trial frame 100 and adjust the temples 250 to fit to himself. Then, the two-dimensional image of the measurement subject 300 is recorded and transmitted to a computing unit for handling the associated information, and then the computing unit obtains the lengths of the temples 250 fitting to the users. Therefore, the customer does not need an optometrist to prescribe a customized frame, and no longer needs to go to a specific place at which the optometrist is on duty, thus lowing the fee for prescribing glasses.

The two-dimensional image of measurement subject 300 may be recorded by any kind of image capturing device. Therefore, if the consumer has the trial frame 100, at any time and any place, the consumer can wear the trial frame 100 and adjust the trial frame 100 to fit to himself, and then the two-dimensional image of the measurement subject 300 can be recorded by his image capturing device and transmitted to the computing unit. Then, the key parameter of the trial frame body 200 can be obtained.

It can be known from the aforementioned measuring process that the trial frame body 200 does not need a precise assembly structure. Only the fixed portion (the connecting portion 251) and the moving portion movable with respect to the fixed portion (the ear portion 252) are required to achieve the measurement. Therefore, the trial frame body 200 may be constructed by a low cost material such as plastic or paper. In addition, because the structure of the trial frame body 200 is simple, instead of moving in small scales with equal intervals with respect to each other, the fixed portion and the moving portion can be designed to continuously move with respect to each other, so as to obtain continuous measurement information.

Because the arrowhead patterns H are disposed above and beneath the fixed points such as the fixed point A and the moving point, and meanwhile there are coordinate differences between the arrowhead patterns H and the fixed points/the moving point in a horizontal direction, the arrowhead patterns H can be used as reference subjects of the fixed points and the moving point, so as to accurately position the fixed points and the moving point in image processing.

By using the aforementioned measurement method, the trial frame 100 can be used to measure different key parameters, such as a distance between eyewires and the nose rests 240, which will be described in the below, and because the measurement principle is the same as what is described above, only differences will be described.

Figure 3A:
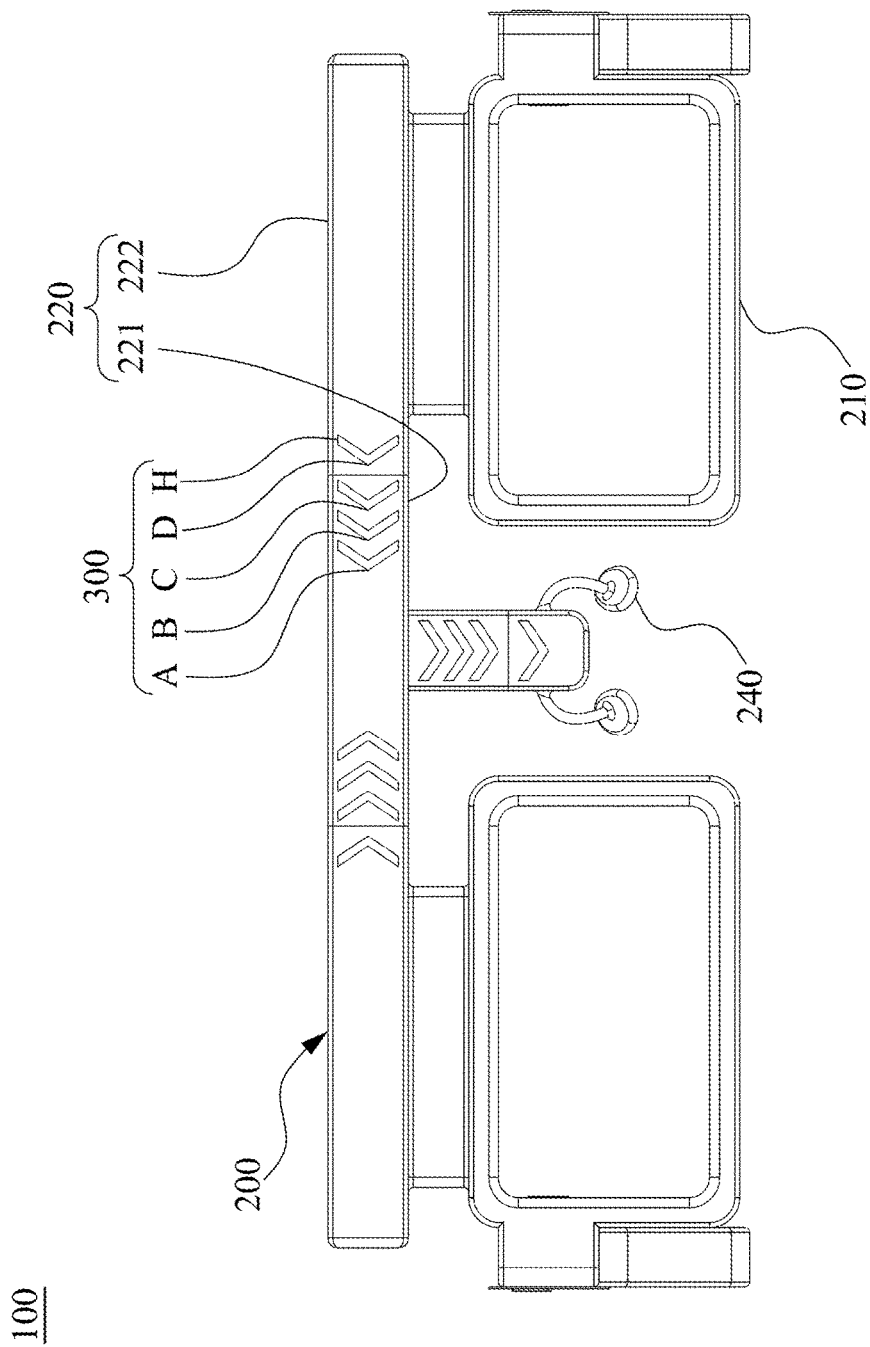
FIG. 3A is a front view of FIG. 1.
Figure 3B:
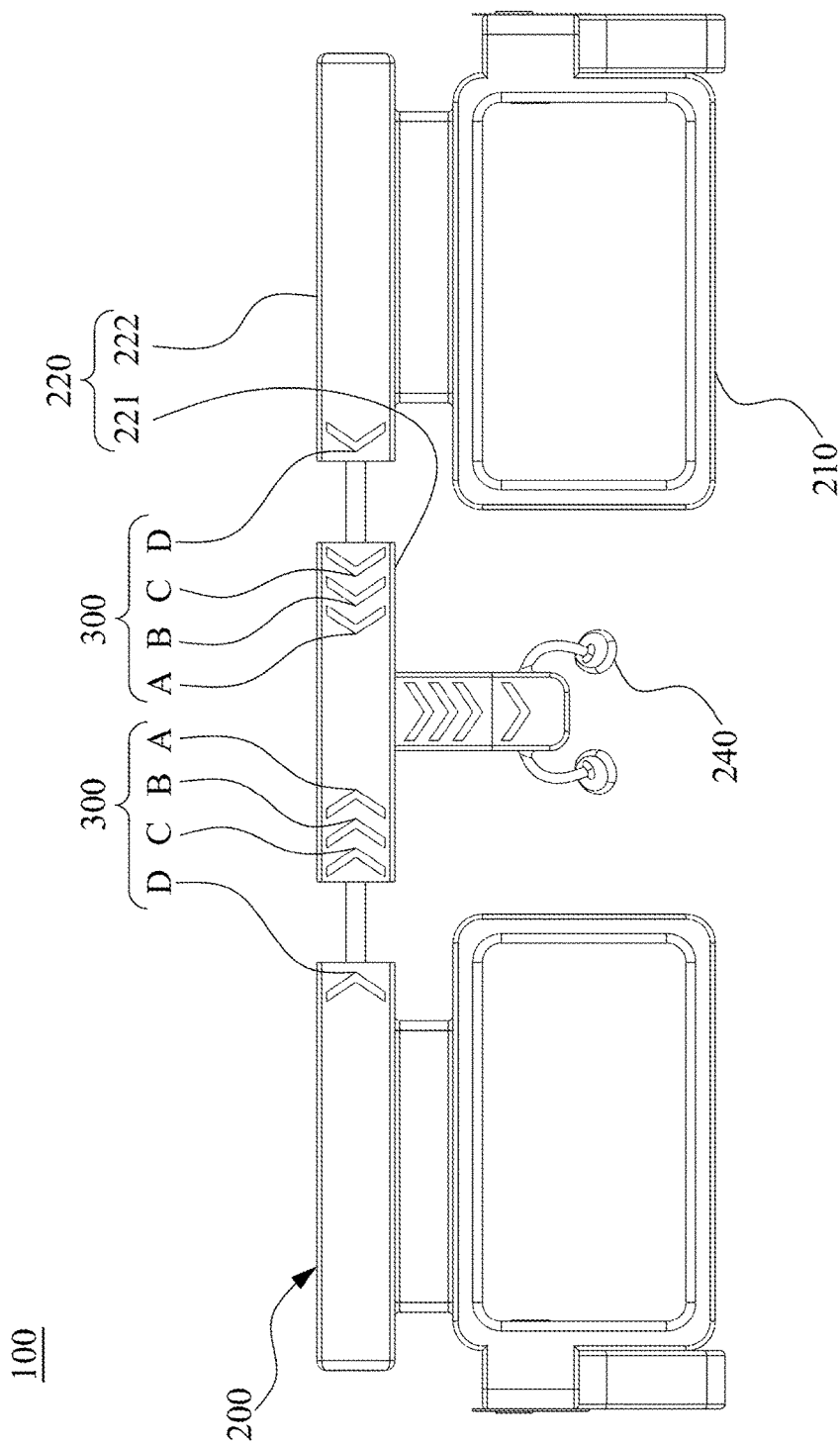
FIG. 3B is a front view of the trial frame of FIG. 1 when a pupil distance measurement ruler is extended.

FIG. 3A is a front view of FIG. 1. FIG. 3B is a front view of the trial frame 100 of FIG. 1 when the pupil distance measurement ruler 220 is extended. As shown in FIG. 3A and FIG. 3B, the pupil distance measurement ruler 220 includes a fixed portion 221 and a pair of moving portions 222 movably connected to the fixed portion 221. The eyewires 210 are respectively connected to the moving portions 222. The measurement subject 300 includes a fixed point A, a fixed point B, a fixed point C, and a moving point D. The fixed points A, B, and C are disposed on the fixed portion 221 with equal intervals between each other, and the moving point D is disposed on one of the moving portions 222. The points A, B, C, and D are disposed on the same straight line. In addition, the number of the measurement subjects 300 may be two, and the measurement subjects 300 may be disposed on the fixed portion 221 and two moving portion 222 at the same time.

Therefore, similar to the aforementioned measuring process, after the user adjusts the pupil distance measurement ruler 220, the two-dimensional image of the measurement subject 300 is recorded, and the distance between the eyewires 210 of the trial frame body 200 can be deduced.

Figure 4A:
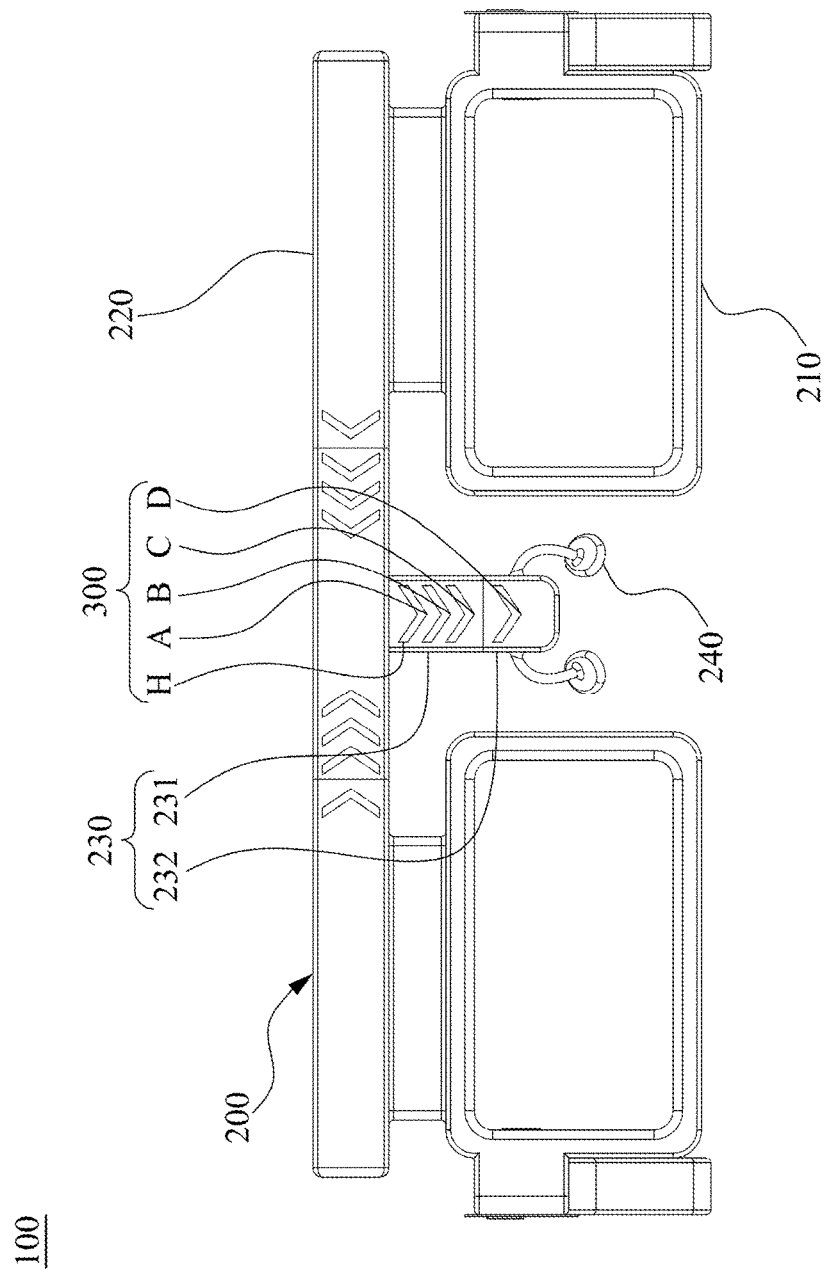
FIG. 4A is another front view of FIG. 1.
Figure 4B:
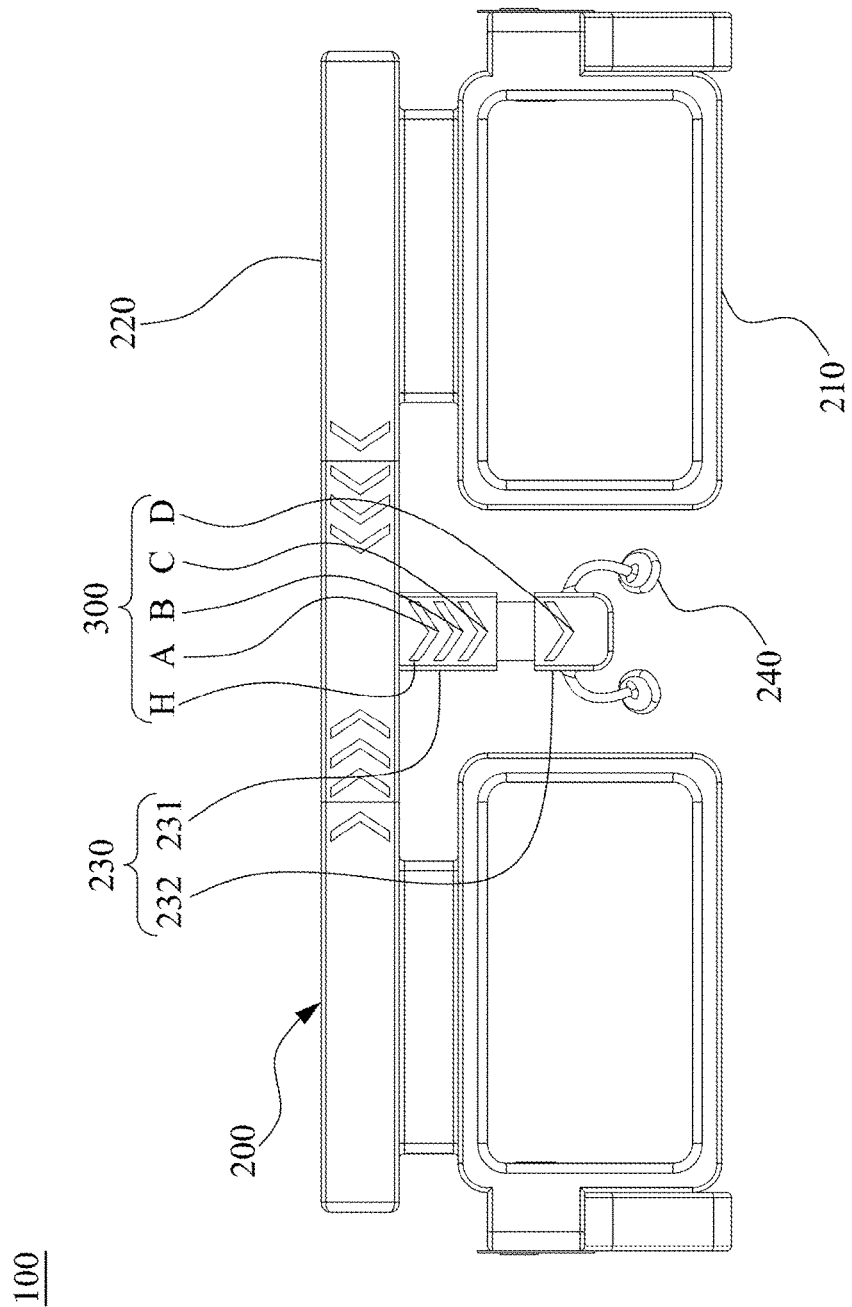
FIG. 4B is a front view of the trial frame of FIG. 1 when a nose bridge measurement ruler is extended.

FIG. 4A is another front view of FIG. 1. FIG. 4B is a front view of the trial frame 100 of FIG. 1 when the nose bridge measurement ruler 230 is extended. As shown in FIG. 4A and FIG. 4B, the nose bridge measurement ruler 230 includes a fixed portion 231 and a moving portion 232 connected to the fixed portion 231. The nose rests 240 are connected to the moving portion 232. The measurement subject 300 includes a fixed point A, a fixed point B, a fixed point C, and a moving point D. The fixed points A, B, and C are disposed on the fixed portion 231 with equal intervals between each other, and the moving point D is disposed on the moving portion 232. The points A, B, C, and D are disposed on the same straight line.

Therefore, similar to the aforementioned measuring process, after the user adjusts the nose bridge measurement ruler 230, the two-dimensional image of the measurement subject 300 is recorded, and the relative position of the nose bridge measurement ruler 230 can be deduced.

By using the aforementioned measurement method or other methods, the trial frame 100 can be used to measure a magnitude of an angle between the eyewires 210 and the temples 250, which is one of the key parameters. Because the measurement principle is partially the same as what is described above, only differences will be described in the below.

Figure 5A:
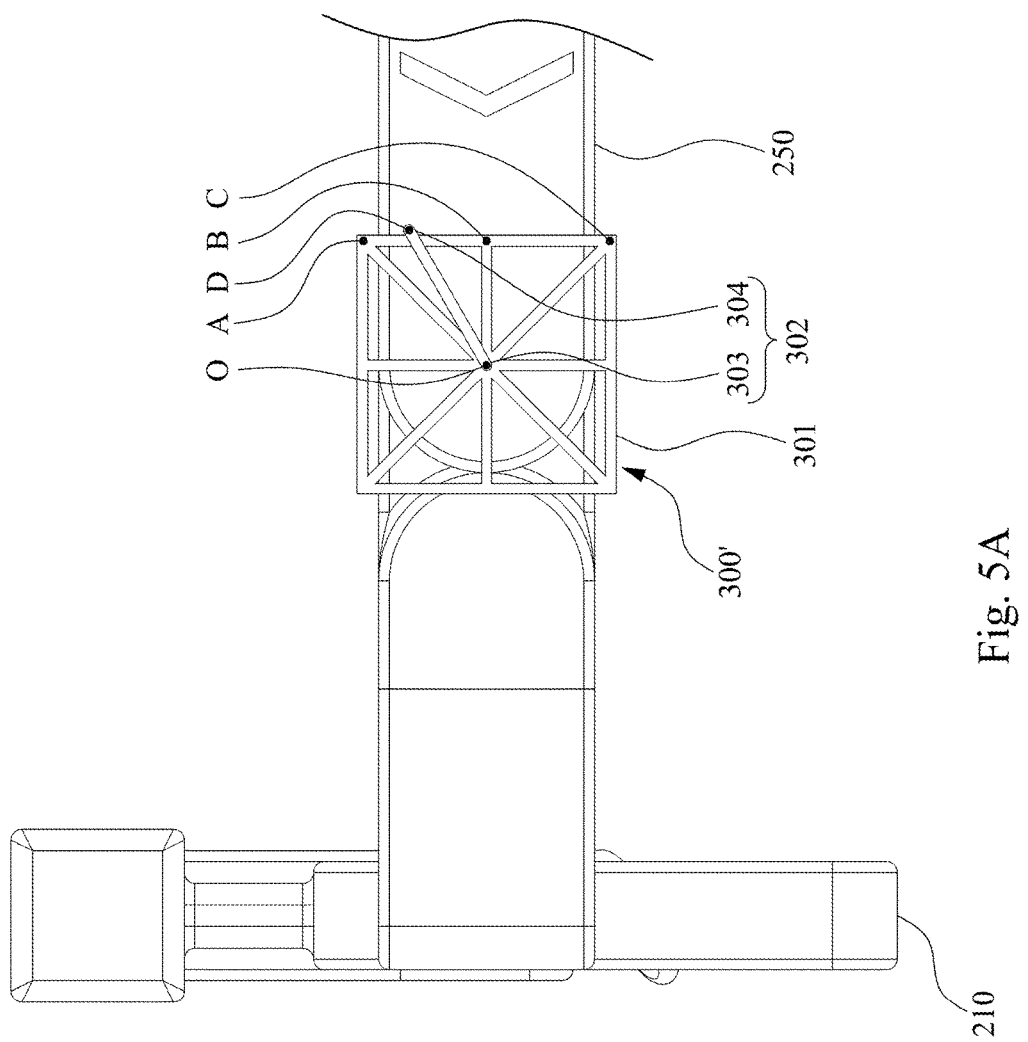
FIG. 5A is a partial side view of FIG. 1.
Figure 5B:
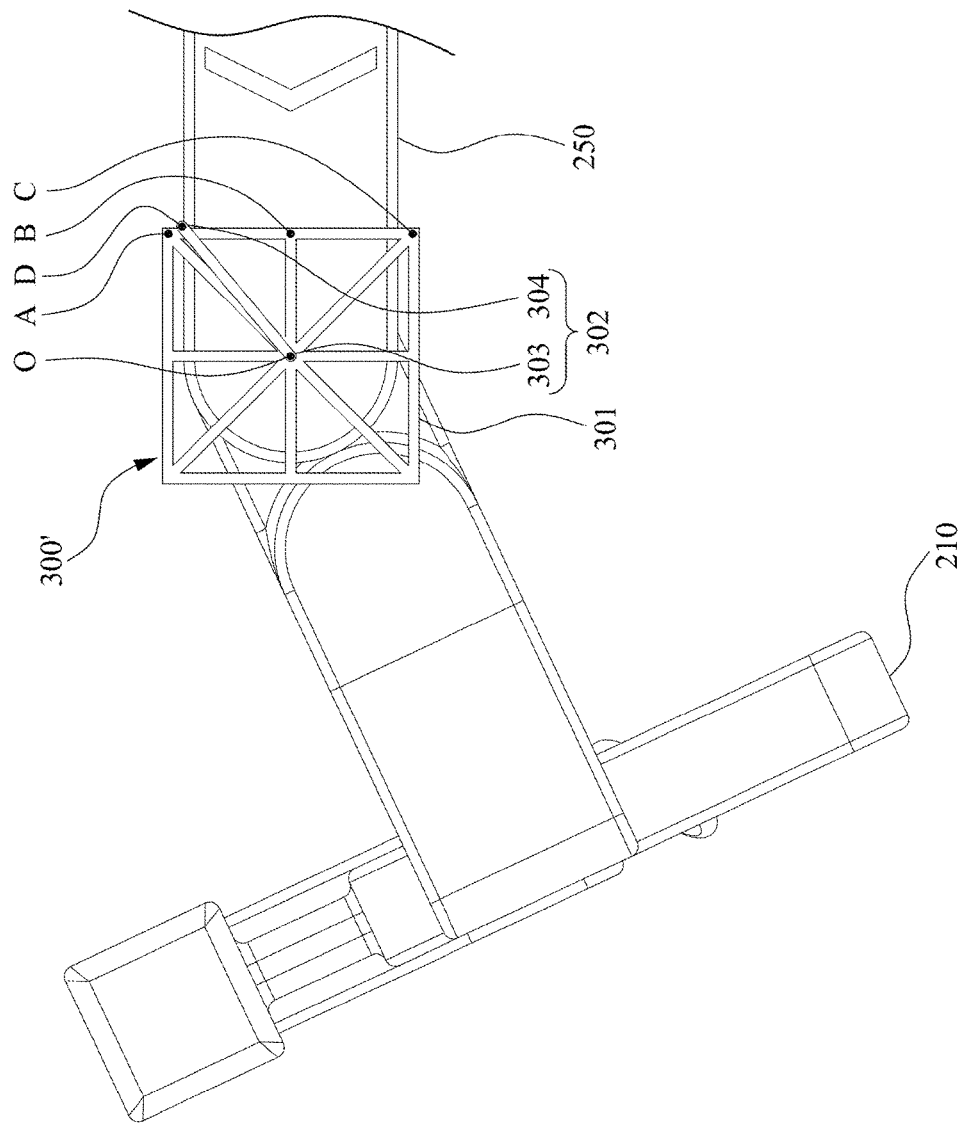
FIG. 5B is a partial side view of the trial frame of FIG. 1 when eyewires rotate with respect to the temples.

FIG. 5A is a partial side view of FIG. 1. FIG. 5B is a partial side view of the trial frame 100 of FIG. 1 when the eyewires 210 rotate with respect to the temples 250. As shown in FIG. 5A and FIG. 5B, the trial frame body 200 may further include an angle measuring module, in which the angle measuring module may be the measurement subject 300'. The eyewires 210 are rotatably connected to the temples 250. The angle measuring module provides information showing an angle relationship between the temples 250 and the eyewires 210.

The measurement subject 300' is fixed to the temples 250. The angle measuring module includes a fixed portion 301 and a moving portion 302 connected to the fixed portion 301. The angle measuring module includes a fixed point A, a fixed point B, a fixed point C, a moving point D, and a fixed point O. The fixed points A, B, and C are disposed on the fixed portion 301 with equal intervals between each other, and the points A, B, and C are disposed on the same straight line. The fixed point O is disposed on the fixed portion 301, and magnitudes of angles ∠AOB and ∠BOC are the same. The moving portion 302 has a first end 303 and a second end 304. The first end 303 of the moving portion 302 is connected to the fixed point O. The moving point D is disposed on the second end 304 of the moving portion 302. The second end 304 is movably connected to the fixed portion 301. The connection portion of the second end 304 and the fixed portion 301, and the fixed points A, B, and C are disposed on the same straight line. The moving portion 302 is fixed to the eyewires 210, such that when the eyewires 210 are rotated with respect to the temples 250, the moving point D moves with respect to the fixed portion 301, and an angle between the moving portion 302 and the eyewires 210 is fixed.

Similar to the aforementioned measuring process, after the user adjusts the angle between the eyewires 210 and the temples 250, the two-dimensional image of the measurement subject 300' is recorded, and the cross ratio R of the points A, B, C, and D is deduced. Then, the relative position of the moving point D can be deduced, and a magnitude of the angle between the moving portion 302 and the temples 250 can be obtained (in the embodiment, because $\overline{OB}$ is parallel to a direction of the temples 250, the angle between the moving portion 302 and the temples 250 is ∠DOB). Because the angle between the moving portion 302 and the eyewire 210 is fixed, the magnitude of the angle between the eyewires 210 and the temples 250 can be obtained.

In the above description, the temples 250 (or the fixed portion 301) are regarded as a fixed reference. However, in a actual situation, the eyewires 210 may be regarded as the fixed reference, i.e., the user fixes the eyewires 210 and then rotates the temples 250 with respect to the eyewires 210 to adjust the angle relation between the temples 250 and the eyewires 210.

Specifically, no fixing structure is disposed between the second end 304 of the moving portion 302 and the fixed portion 301. The second end 304 movably contacts the fixed portion 301, and the second end 304 and the fixing portion 301 are substantially located on the same plane. In other words, the moving portion 302 is a column rotating with the fixed point O as the pivot, and is attached on the fixed portion 301.

When the image processing is performed, coordinates of the position of the moving point D in the image is an intersection point of the moving portion 302 and $\overline{AC}$. Because the moving portion 302 in fact is a column with a width, two edges of the moving portion 302 can be regarded as the references at the same time to achieve accurate measurement when positions of the moving point D is determined.

Because the relative positions of the points A, B, C, and D of the measurement subject 300' of FIG. 5A and FIG. 5B are different from the aforementioned embodiments, the definition of the cross ratio R is changed to the following equation accordingly:

$$R = \frac{\overline{ADBC}}{\overline{BDAC}}$$

In other embodiments, the angle measuring modules may be different, and are described as follows.

Figure 6:
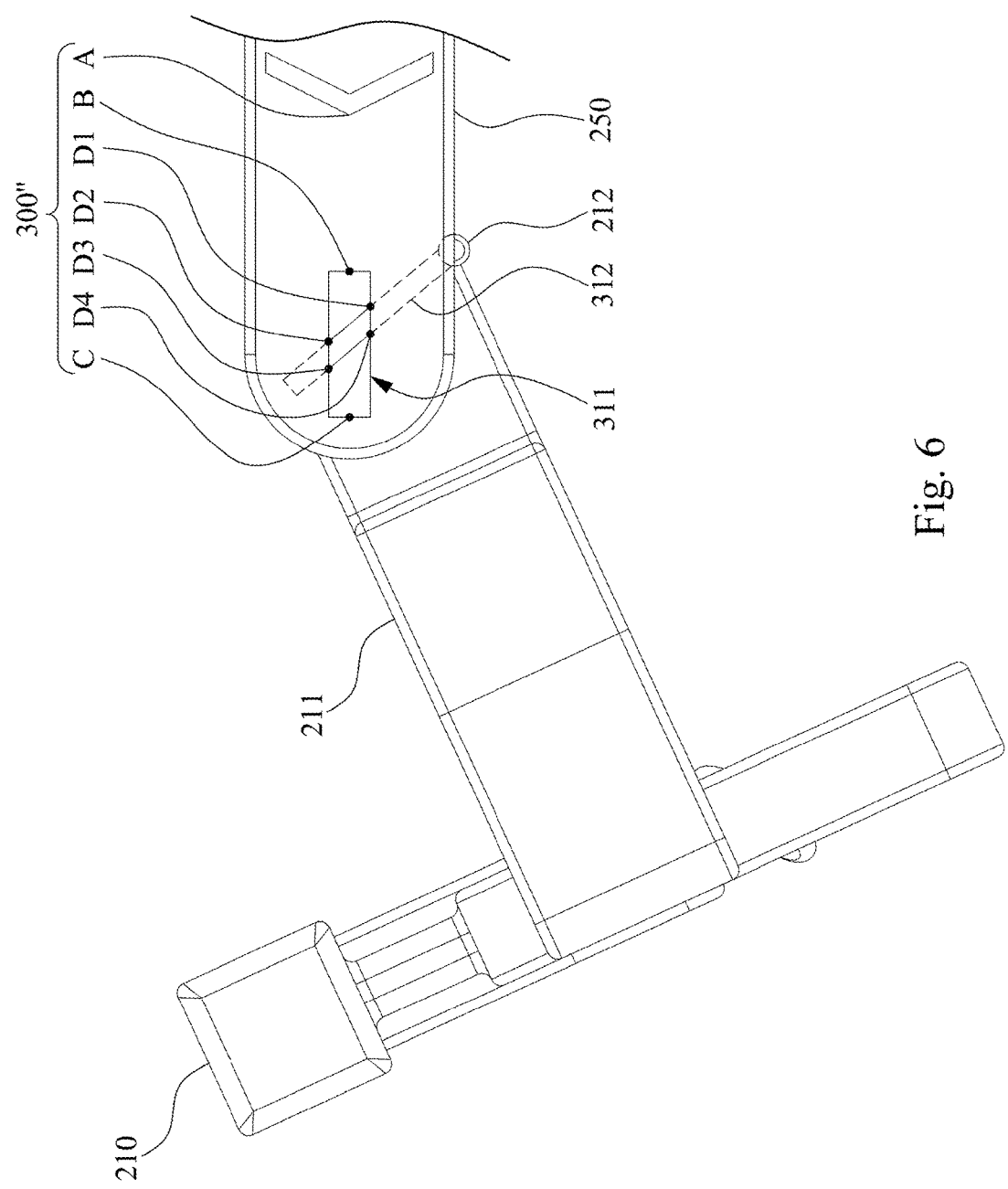
FIG. 6 is a partial side view of the trial frame according to another embodiment of this invention.

FIG. 6 is a partial side view of the trial frame 100 according to another embodiment of this invention. As shown in FIG. 6, the angle measuring module is the measurement subject 300", and the angle measuring module includes an opening 311 and the moving portion 312. The eyewires 210 further includes an extended portion 211 and a pivot 212. The temples 250 are rotatably connected to the extended portion 211 of the eyewires 210 via the pivot 212. The opening 311 is disposed on the temples 250, and the opening 311 is strip-shaped. Longer edges of the opening 311 are parallel to the temples 250. The pivot 212 is disposed above or beneath the opening 311. The moving portion 312 is fixed to the eyewires 210. The opening 311 exposes a portion of the moving portion 312. When the eyewires 210 rotates with respect to the temples 250, the eyewires 210 rotate with the pivot 212. When the rotation angle is different, the exposed portion of the moving portion 312 in the opening 311 is different.

The angle measuring module includes a fixed point A, a fixed point B, a fixed point C, a moving point D1, a moving point D2, a moving point D3, and a moving point D4. The fixed point A may be the fixed point A of FIG. 2. The fixed point B and the fixed point C may be midpoints of the shorter edges of the opening 311. The moving points D1, D2, D3, and D4 are respectively four vertices of a parallelogram exposed by the opening 311 of the moving portion 312.

Similar to the aforementioned measuring process, after the user adjusts the angle between the eyewires 210 and the temples 250, the two-dimensional image of the measurement subject 300" is recorded. Then, by selecting one of the moving points D1, D2, D3, and D4 collocated with the fixed points A, B, and C, the corresponding cross ratios R may be deduced. Then, the positions of the moving points D1, D2, D3, and D4 relative to other points can be deduced. Because the spatial configuration of the pivot 212 and the opening 311 is known, the angle between the moving portion 312 and the temples 250 can be obtained by the spatial configuration of the pivot 212, the opening 311, and the moving points. Because the angle between the moving portion 312 and the eyewire 210 is fixed, the angle between the eyewires 210 and the temples 250 can be obtained.

In the embodiment, four cross ratios R may be deduced, so that there are more reference information for the image processing and the angle deduction, thus obtaining more accurate result.

It is noted that though the moving points such as the moving point D1 and the fixed points A, B, and C are not on the same straight line, the moving points and the fixed points can be assumed to be on the same straight line, since a length of the short edges of the opening 311 much smaller than the distances between fixed points.

Because the relative positions of the fixed points A, B, and C, and the moving points D1, D2, D3, and D4 of the measurement subject 300" of FIG. 6 are different from the aforementioned embodiments, the definition of the cross ratio R is changed to the following equation accordingly:

$$R = \frac{\overline{ABCDx}}{\overline{BDxAC}} \quad (Dx \text{ can be } D1, D2, D3 \text{ or } D4)$$

Figure 7:
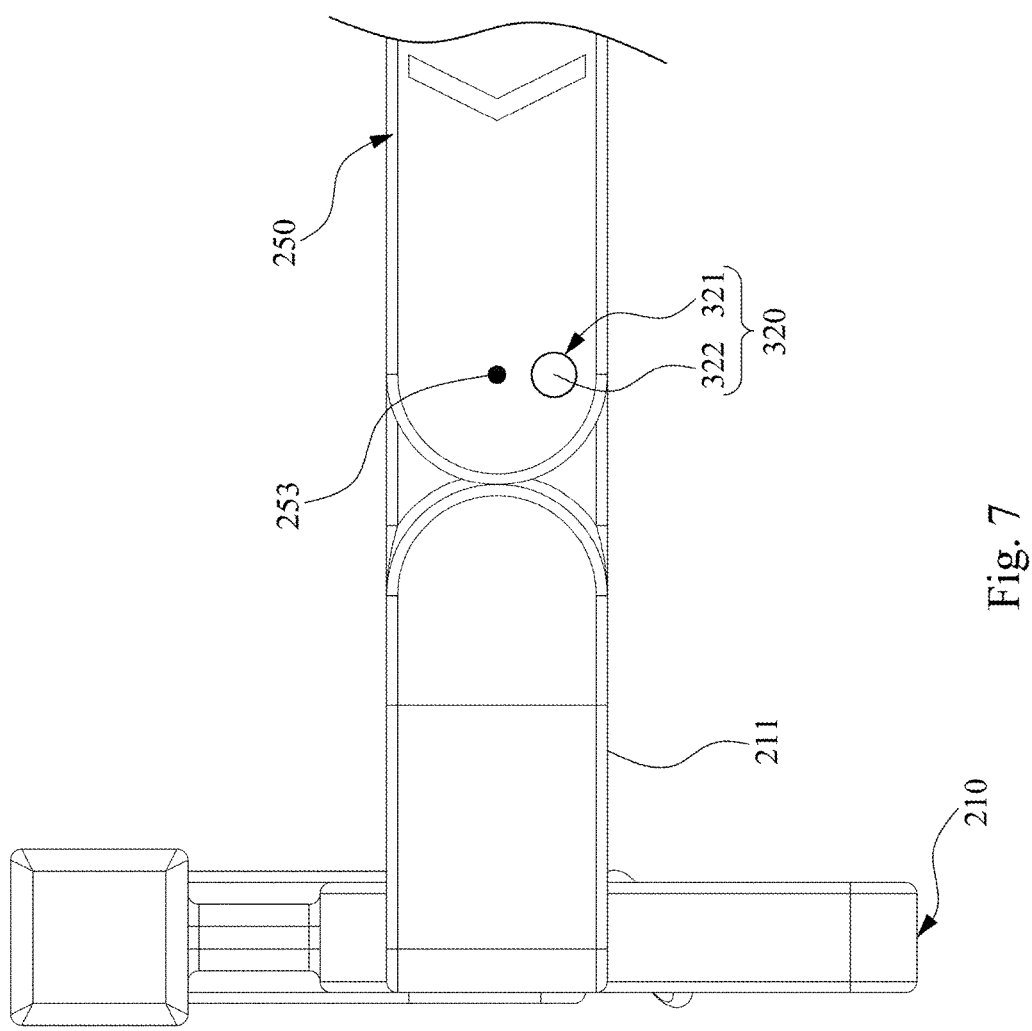
FIG. 7 is a partial side view of the trial frame according to another embodiment of this invention.

FIG. 7 is a partial side view of the trial frame 100 according to another embodiment of this invention. As shown in FIG. 7, the angle measuring module is the angle-color detection module 320. The angle-color detection module 320 includes an opening 321 and a color display region 322. The eyewires 210 further includes the extended portion 211. The temples 250 further include a pivot 253. The temples 250 are rotatably connected to the extended portion 211 of the eyewires 210 via the pivot 253. The opening 321 is disposed on the temples 250 and exposes a portion of the extended portion 211 to form the color display region 322. When the eyewires 210 rotate with respect to the temples 250, the eyewires 210 rotate with the pivot 253. When the rotation angle is different, the color display region 322 exposes different portions of the extended portion 211. If different colors are painted on different portons of the extended portion 211, the color display region 322 shows different colors when the rotation angle is different. Therefore, by knowing the color shown in the color display region 322, the magnitude of the angle between the eyewires 210 and the temples 250 can be known.

Figure 8:
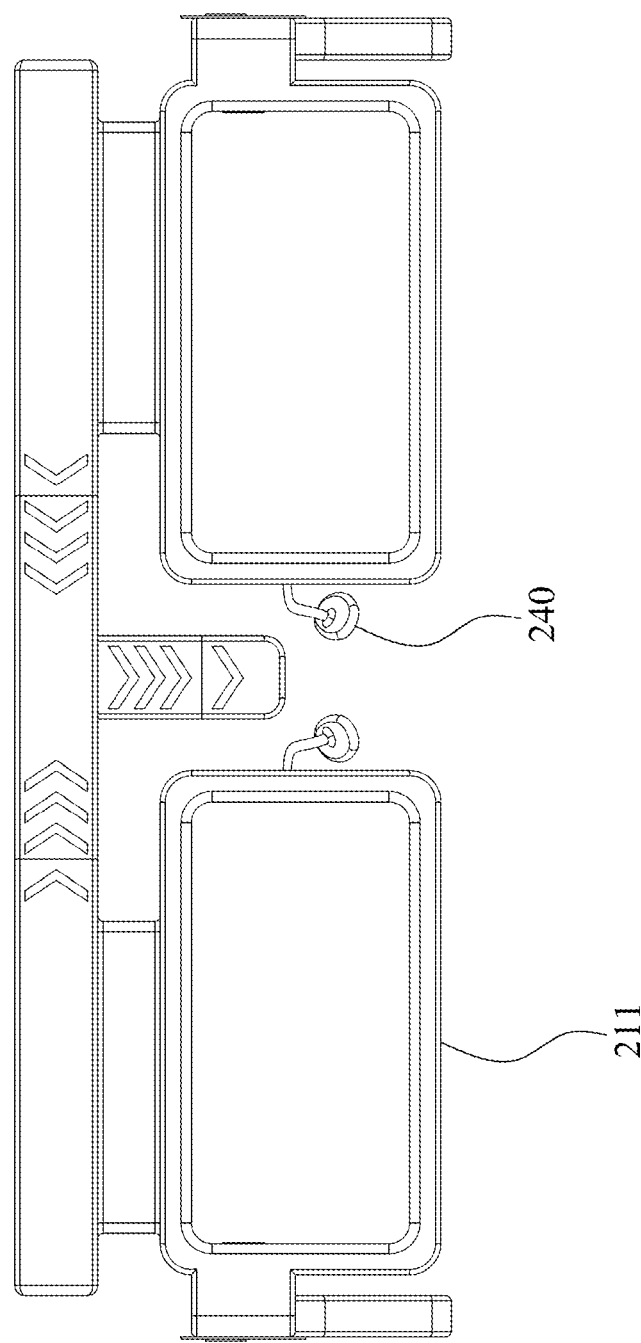
FIG. 8 is a partial side view of the trial frame according to another embodiment of this invention.

FIG. 8 is a partial side view of the trial frame 100 according to another embodiment of this invention. As shown in FIG. 8, the nose rests 240 is directly connected to the eyewires 210. The other portions of the trial frame 100 are similar to those of the aforementioned embodiments.

Figure 9:
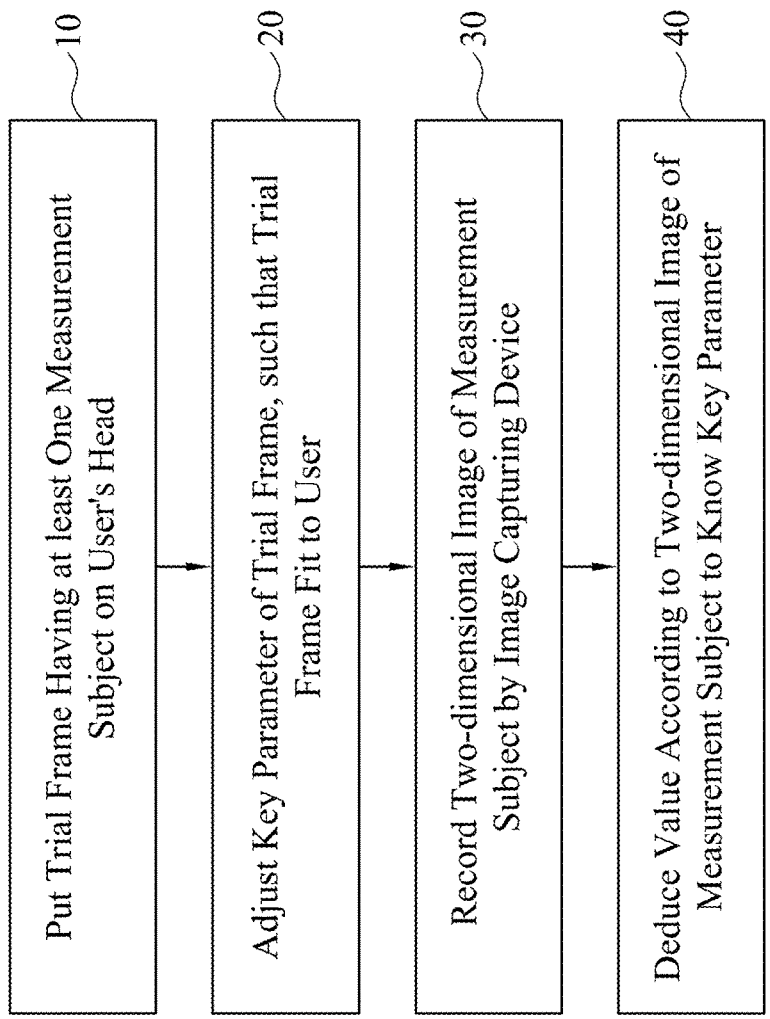
FIG. 9 is a flowchart of a method for measuring a key parameter of the trial frame according to one embodiment of this invention.

FIG. 9 is a flowchart of a method for measuring the key parameter of the trial frame 100 according to one embodiment of this invention. As shown in FIGS. 1 to 9, a method for measuring the key parameter of the trial frame 100 is provided. Step 10 is performed for putting the trial frame 100 having at least one measurement subject 300 on a user's head, in which the measurement subject 300 has the visual invariant geometric characteristic which deduces a value (the cross ratio R) corresponding to the key parameter of the trial frame 100. Step 20 is performed for adjusting the key parameter of the trial frame 100, such that the trial frame 100 fits to the user. Step 30 is performed for recording the two-dimensional image of the measurement subject 300 by the image capturing device. Step 40 is performed for deducing the value according to the two-dimensional image of the measurement subject 300 to know the key parameter.

Specifically, the trial frame 100 includes a fixed portion and a moving portion. A spatial configuration of the fixed portion and the moving portion determines the key parameter of the trial frame 100. The fixed points A, B, and C are disposed on the fixed portion with equal intervals between each other, and the moving point D is disposed on the moving portion. The points A, B, C, and D are disposed on the same straight line.

By disposing the measurement subject 300 having the visual invariant geometric characteristic on the trial frame body 200, the key parameter of the trial frame 100 can be deduced by using the two-dimensional image of the measurement object 300 recorded by the image capturing device when the trial frame 100 fits the user. Therefore, the consumer who desires to prescribe glasses does not need to attend a specific place at which the optometrist is on duty for measuring the key parameter of the trial frame 100. By transmitting some pictures of the trial frame 100 to the computer, the key parameter can be obtained, and thus the fee for prescribe glasses is lowered as well.

All the features disclosed in this specification (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means for" performing a specified function, or "step for" performing a specific function, is not to be interpreted as a "means" or "step" clause as specified in 35 U.S.C. § 112, 6th paragraph. In particular, the use of "step of" in the claims herein is not intended to invoke the provisions of 35 U.S.C. § 112, 6th paragraph.

What is claimed is:

1. A trial frame, comprising:
   a trial frame body having at least one key parameter, the trial frame body comprising:
      a measurement ruler comprising a first fixed portion and a pair of first moving portions respectively movably connected to two ends of the first fixed portion, wherein the first fixed portion has a longitudinal axis, and the first moving portions are configured to move along the longitudinal axis; and
      a pair of eyewires respectively physically connected to the first moving portions, wherein the first moving portions are configured to adjust a distance between the eyewires; and
   at least one measurement subject which has a visual invariant geometric characteristic and is disposed on the trial frame body for collaborating with a measurement method, wherein a two-dimensional image of the measurement subject is recorded by an image capturing device when the trial frame body fits to a user, the measurement subject comprises three fixed points on the first fixed portion and one moving point on one of the first moving portions, the four points are disposed on the same straight line and on the same plane, the straight line is superimposed on the plane, and the key parameter is deduced from the two-dimensional image of the measurement subject.

2. The trial frame of claim 1, wherein the trial frame body further comprises:
   a pair of nose rests connected to the eyewires; and
   a pair of temples, comprising:
      a pair of connecting portions connected to the eyewires; and
      a pair of ear portions moveably connected to the connecting portions respectively;
   wherein the measurement subject comprises a fixed point A, a fixed point B, a fixed point C, and a moving point D; the fixed point A, the fixed point B, and the fixed point C are disposed on one of the connecting portions with equal intervals between each other; the moving point D is disposed on one of the ear portions; and the point A, the fixed point B, the fixed point C, and the moving point D are disposed on the same straight line.

3. The trial frame of claim 1,
   wherein the three fixed points are disposed with equal intervals between each other.

4. The trial frame of claim 1, wherein the trial frame body further comprises:
   a nose bridge measurement ruler connected to the first fixed portion of the measurement ruler, wherein the nose bridge measurement ruler comprises a second fixed portion and a second moving portion connected to the second fixed portion;
   a pair of nose rests connected to the second moving portion; and
   a pair of temples connected to the eyewires;

wherein the measurement subject comprises a fixed point A, a fixed point B, a fixed point C, and a moving point D, and the fixed point A, the fixed point B, and the fixed point C are disposed on the second fixed portion with equal intervals between each other; the moving point D is disposed on the second moving portion; and the fixed point A, the fixed point B, the fixed point C, and the fixed point D are disposed on the same straight line.

5. The trial frame of claim 1, wherein the trial frame body further comprises:
a pair of temples, wherein the eyewires rotatably connected to the temples;
a pair of nose rests respectively connected to the eyewires; and
an angle measuring module fixed to the temples; wherein the angle measuring module comprises a second fixed portion and a second moving portion connected to the second fixed portion; the angle measuring module comprises a fixed point A, a fixed point B, a fixed point C, a moving point D, and a fixed point O; the fixed point A, the fixed point B, and the fixed point C are disposed on the second fixed portion with equal intervals between each other; the point A, the fixed point B, and the fixed point C are disposed on the same straight line; the fixed point O is disposed on the second fixed portion; an angle ∠AOB and an angle ∠BOC have the same magnitudes; the second moving portion has a first end and a second end; the first end of the second moving portion is connected to the fixed point O; the moving point D is disposed on the second end of the second moving portion; the second end is movably connected to the second fixed portion; the connection portion of the second end and the second fixed portion, the fixed point A, the fixed point B, and the fixed point C are disposed on the same straight line; and the second moving portion is fixed to the eyewires, such that when the eyewires are rotated with respect to the temples, the moving point D moves with respect to the second fixed portion, and an angle between the second moving portion and the eyewires is fixed.

6. The trial frame of claim 1, wherein the trial frame body further comprises:
a pair of temples, wherein the eyewires rotatably connected to the temples;
a pair of nose rests respectively connected to the eyewires; and
an angle measuring module for providing an information showing an angle relationship between the temples and the eyewires.

7. A method for measuring a key parameter of a trial frame, the method comprising:
putting the trial frame of claim 1 on the user's head;
adjusting the key parameter of the trial frame for fitting the trial frame to the user;
recording the two-dimensional image of the measurement subject by the image capturing device; and
deducing a cross ratio corresponding to the key parameter of the trial frame according to the two-dimensional image of the measurement subject, thereby determining the key parameter of the trial frame, wherein the cross ratio is the same when the two-dimensional image of the measurement subject is taken in different recording angles and different recording distances.

8. The method of claim 7, wherein the measurement subject comprises a fixed point A, a fixed point B, a fixed point C, and a moving point D, and the cross ratio R is deduced from the following mathematical relationship:

$$R = \frac{\overline{ABCD}}{\overline{BCAD}}.$$

9. The method of claim 8, wherein the trial frame further comprises a second fixed portion and a second moving portion; a spatial configuration of the second fixed portion and the second moving portion determines the key parameter of the trial frame; the fixed point A, the fixed point B, and the fixed point C are disposed on the second fixed portion with equal intervals between each other; the moving point D is disposed on the second moving portion, the fixed point A, the fixed point B, the fixed point C, and the moving point D are disposed on the same straight line and on the same plane, and the straight line is superimposed on the plane.

10. The trial frame of claim 1, wherein the trial frame further comprises a nose bridge measurement ruler physically connected to the first fixed portion of the measurement ruler, and the nose bridge measurement ruler is between the eyewires.

11. The trial frame of claim 10, wherein the nose bridge measurement ruler has a second fixed portion physically connected to the first fixed portion of the measurement ruler and a second moving portion movably connected to the second fixed portion, and the second moving portion is configured to move along a direction perpendicular to the longitudinal axis of the first fixed portion.

* * * * *

UNITED STATES PATENT AND TRADEMARK OFFICE
CERTIFICATE OF CORRECTION

PATENT NO. : 10,130,252 B2
APPLICATION NO. : 14/481901
DATED : November 20, 2018
INVENTOR(S) : Jen-Hui Chuang et al.

Page 1 of 1

It is certified that error appears in the above-identified patent and that said Letters Patent is hereby corrected as shown below:

On the Title Page

The foreign priority date should be Jun. 17, 2014, rather than Jun. 11, 2014.

Signed and Sealed this
Twenty-second Day of January, 2019

Andrei Iancu
*Director of the United States Patent and Trademark Office*